(12) United States Patent
Kadokura

(10) Patent No.: US 8,192,365 B2
(45) Date of Patent: *Jun. 5, 2012

(54) ULTRASONIC PROBE

(75) Inventor: Masahiko Kadokura, Kanagawa (JP)

(73) Assignee: Panasonic Corporation, Osaka (JP)

( * ) Notice: Subject to any disclaimer, the term of this patent is extended or adjusted under 35 U.S.C. 154(b) by 1230 days.

This patent is subject to a terminal disclaimer.

(21) Appl. No.: 10/596,658

(22) PCT Filed: Dec. 21, 2004

(86) PCT No.: PCT/JP2004/019099
§ 371 (c)(1),
(2), (4) Date: Jun. 20, 2006

(87) PCT Pub. No.: WO2005/060833
PCT Pub. Date: Jul. 7, 2005

(65) Prior Publication Data
US 2009/0143682 A1 Jun. 4, 2009

(30) Foreign Application Priority Data
Dec. 22, 2003 (JP) ................................. 2003-425352

(51) Int. Cl.
*A61B 8/14* (2006.01)
(52) U.S. Cl. .............. 600/459; 73/584; 73/587; 73/593; 73/660; 73/661
(58) Field of Classification Search .................. 600/459; 73/584, 587, 593, 607, 618–620, 625, 660–661; 8/101, 107, 111, 400, 405–406, 428–429, 8/431; 132/202, 204–211
See application file for complete search history.

(56) References Cited

U.S. PATENT DOCUMENTS

| 4,913,158 | A | 4/1990 | Kikuchi et al. | |
| 2002/0062080 | A1* | 5/2002 | Okawa et al. | 600/459 |
| 2004/0266574 | A1* | 12/2004 | Jinno et al. | 474/153 |

FOREIGN PATENT DOCUMENTS

| JP | 62-197308 U | 12/1987 |
| JP | 8-168490 | 7/1996 |
| JP | 10-174686 | 6/1998 |
| JP | 10-179588 | 7/1998 |
| JP | 2001-140990 | 5/2001 |
| JP | 2002-153464 | 5/2002 |

OTHER PUBLICATIONS

Microfilm of the specification and drawings annexed to the request of Japanese Utility Model Application No. 87077/1986 (Laid-open No. 197308/1987), Matsushita Electric Industrial Co., Ltd., Dec. 25, 1987, Full Text; all drawings.
Full International Search Report from International Publication No. WO 2005-060833A1.

* cited by examiner

*Primary Examiner* — Brian Casler
*Assistant Examiner* — Daniel Huntley
(74) *Attorney, Agent, or Firm* — Pearne & Gordon LLP

(57) ABSTRACT

An ultrasonic probe is provided that is capable of preventing the probe's position from being displaced due to wire slippage on a drive pulley and a swing pulley while swinging. The ultrasonic probe includes an ultrasonic transducer unit emitting ultrasonic waves while swinging. Furthermore, a wire is attachable to the ultrasonic probe, which allows for the adjustment of a position angle of an ultrasonic transducer unit in swing operation without the use of a position angle sensor.

18 Claims, 9 Drawing Sheets

ULTRASONIC PROBE

TECHNICAL FIELD

The present invention relates to an ultrasonic probe constituted to have an ultrasonic transducer unit suited for being inserted into a cavity of a living body for emitting ultrasonic waves into an organism of the living body and receiving echo signals therefrom.

BACKGROUND ART

As far as ultrasonic probes of recent years are concerned, a variety of types have been hitherto developed. A conventional ultrasonic probe will be explained by using FIGS. 7 and 8. FIG. 7 is a drawing illustrating a configuration of a conventional ultrasonic probe. FIG. 8 is a view of the ultrasonic probe shown in FIG. 7 as seen from the direction of an arrow 101. As shown in FIG. 7, the ultrasonic probe is constituted to have a grip section 1 and an insert section 2, and the insert section 2 has a configuration including a tip section 3 that in turn includes a base section 3a. A motor 5, and a drive pulley 102 which is swingably or rotatably driven by the motor 5 are incorporated inside the grip section 1. Additionally, a wire drive mechanism 100 which transmits power to a swing pulley 7 by using a wire 8 transmitting the power by the swinging or rotation of the drive pulley 102, the swing pulley which swings around a rotation shaft 9 by the power resulting from the swinging or rotation of the drive pulley 102 transmitted through the wire 8, and an ultrasonic transducer unit 4 operated by the swinging of the swing pulley 7, are incorporated in the interior of the insert section 2. Moreover, as shown in FIG. 8, the ultrasonic probe includes a position angle sensor 103, which detects the position angle of the ultrasonic transducer unit 4. Such an ultrasonic probe is disclosed in Patent document 1 indicated below.

Patent document 1: Japanese Patent Application Publication No. 10(1998)-179588 (FIG. 3)

Nevertheless, in the ultrasonic probe disclosed in Patent document 1, there has been such a problem that the positional displacement occurs due to the slippage of wire 8 on the drive pulley 102 and the swing pulley 7 while swinging. Moreover, since a mechanism had not been included which adjusts the origin position angle of the ultrasonic transducer unit 4 in its swing operation when the wire 8 is attached to the drive pulley 102 and the swing pulley 7, there has been such a problem that a position angle sensor 103, which detects the position angle of the swing pulley 7 must have been incorporated. Furthermore, there has been a problem such that the wire 8 used became long.

DISCLOSURE OF THE INVENTION

The present invention was made to solve the aforementioned various problems, and it is an object to provide an ultrasonic probe, which is capable of preventing an occurrence of position displacement thereof due to the slippage of a wire on a drive pulley and a swing pulley during swinging, enabling the easy mounting of the wire thereto while adjusting the origin position angle of an ultrasonic transducer unit in swing operation without using any position angle sensor, and enabling the wire length to be shortened.

According to the present invention, in order to achieve the aforementioned object, there is provided an ultrasonic probe, which comprises an ultrasonic transducer unit that emits ultrasonic waves during swinging thereof, a motor that generates a power for swinging the aforementioned ultrasonic transducer unit, a first power transmission means connected to the rotating shaft of the aforementioned motor to transmit the power, a drive means connected to the aforementioned first drive transmission means to be rotated by the transmitted power, a second cable-like power transmission means transmitting the power by the rotation of the aforementioned drive means, a swing means on which the aforementioned ultrasonic transducer unit is mounted and capable of swinging the aforementioned ultrasonic transducer unit with the power from the rotation of the aforementioned drive means transmitted through the second drive transmission means, a first fixing means for fixing thereto both ends of the second power transmission means, the first fixing means being fixed to the swing means together with the fixed second power transmission means, and a second fixing means for fixing, to the aforementioned drive means, an opposite end of the second fixing means that is arranged to be opposed to a fixed end of the second power transmission means which is formed in a ring-shape due to fixing at the fixed end to the first fixing means. According to this configuration, it is possible to prevent the position of the wire which is the cable-like second power transmission means from being displaced due to the slippage of the wire on a drive pulley which is the drive means and a swing pulley which is the swing means during swinging of the ultrasonic transducer unit, easy mounting of the wire can be achieved while adjusting the origin position angle in the swing operation of the ultrasonic transducer unit without using a position angle sensor, and shortening of the length of the wire can be realized.

Moreover, in a preferred embodiment of an ultrasonic probe of the present invention, the aforementioned first fixing means is composed of a material being deformed by an external force and having a plurality of penetrating holes which are communicated with one another inside thereof, wherein pressure is applied to the aforementioned first fixing means under a condition where both ends of the aforementioned second power transmission means are drawn from one of the aforementioned plurality of penetrating holes to another hole, fixed to be one portion together with the second power transmission means, and fixed to the swing means together with the fixed second power transmission means. According to this configuration, it is possible to reduce the lift and the slippage of wire on the swing pulley.

Moreover, in a preferred embodiment of the present invention, the second fixing means of the ultrasonic probe of the present invention is comprised of a screw that fixes the second power transmission means to the drive means. According to this configuration, it is possible to adjust and set coincidence between the origin position angle of the ultrasonic transducer unit and the origin position angle of the motor.

Furthermore, in another preferred embodiment of the present invention, the aforementioned screw of the ultrasonic probe of the present invention is provided with a plate-like portion capable of preventing the second power transmission means from being damaged through the clamping of the aforementioned screw. According to this configuration, it is possible to prevent the wire that constitutes the second power transmission means from being damaged by threadedly clamping the screw.

The ultrasonic probe of the present invention having the aforementioned configuration can prevent the position of the wire from being displaced due to the slippage of the wire on the drive pulley and the swing pulley during swinging, enables easy mounting of the wire thereon while adjusting the origin position angle of an ultrasonic transducer unit in its swing operation without employing a position angle sensor, and enables shortening of the length of wire.

BEST MODE FOR CARRYING OUT THE INVENTION

First Embodiment

Figure 1:
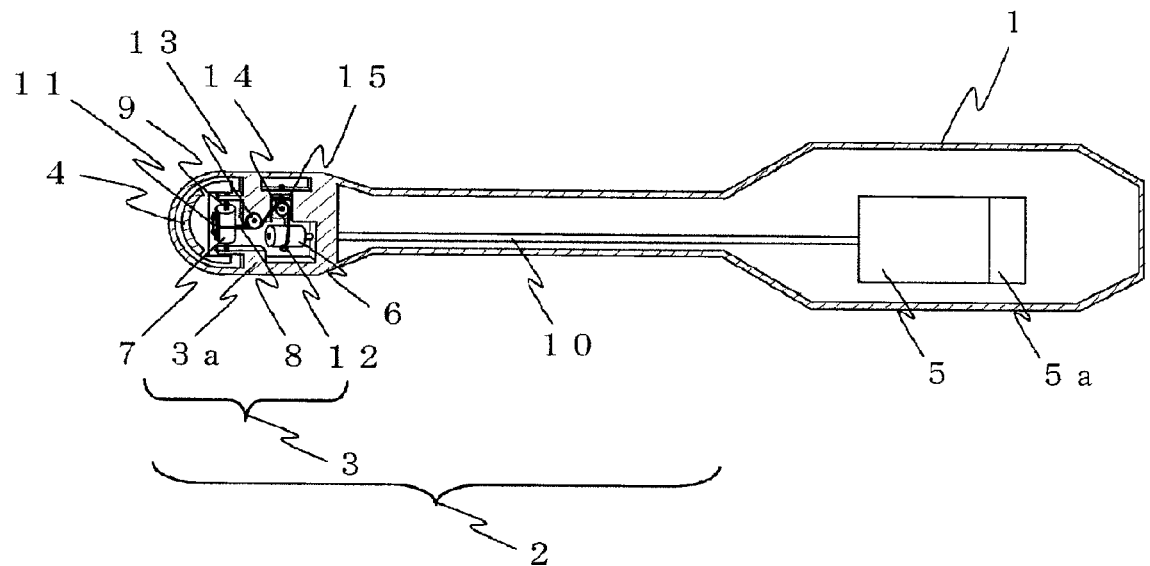
FIG. 1 A schematic view illustrating a configuration of an ultrasonic probe according to the first embodiment of the present invention.
Figure 2:
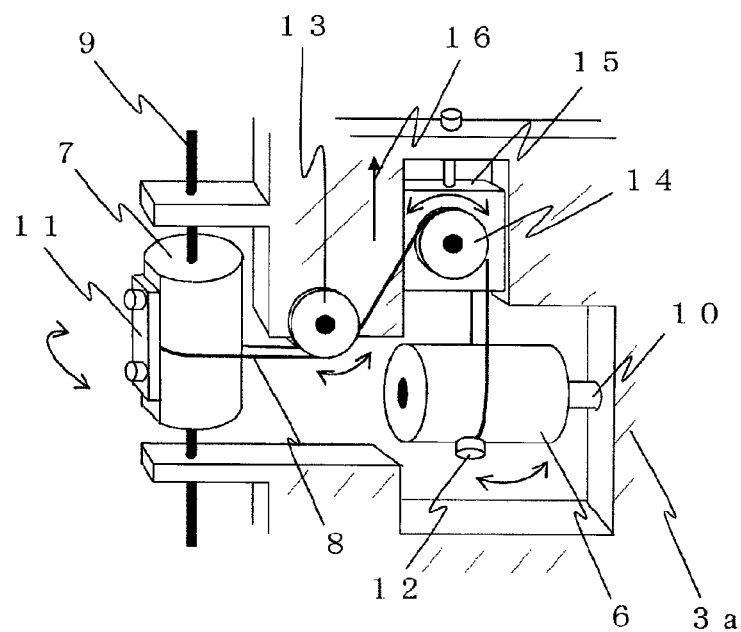
FIG. 2 A schematic view illustrating an internal configuration of a tip section of the ultrasonic probe according to the first embodiment of the present invention.
Figure 3A:
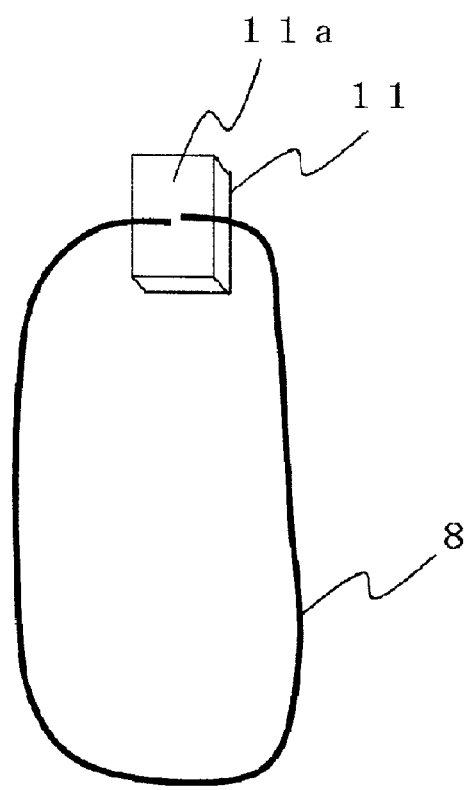
FIG. 3A A schematic view illustrating a wire, which is fixed to a fixed side wall of a connecting section in the ultrasonic probe according to the first embodiment of the present invention.
Figure 3B:
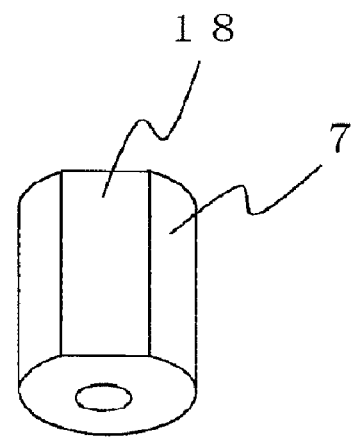
FIG. 3B A schematic view illustrating a cut section of a swing pulley in the ultrasonic probe according to the first embodiment of the present invention.
Figure 3C:
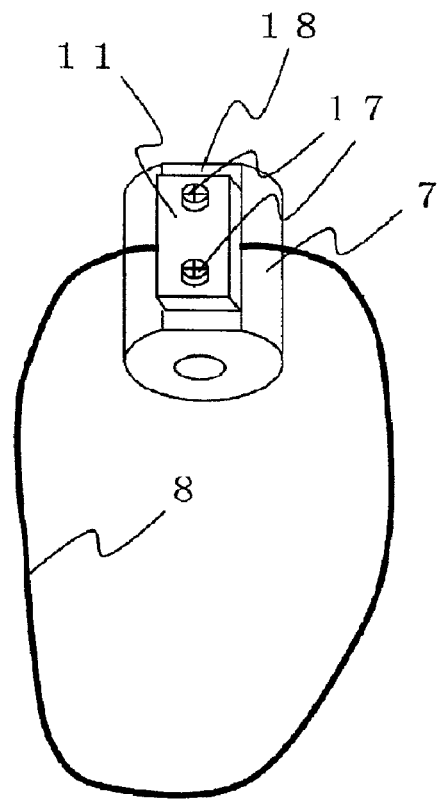
FIG. 3C A schematic view illustrating a connecting section where the wire is fixed to the fixed side wall being attached to the cut section of the swing pulley in the ultrasonic probe according to the first embodiment of the present invention.

Hereinafter, an ultrasonic probe of the first embodiment of the present invention will be explained referring to FIGS. 1 to 4B. FIG. 1 is a view illustrating a configuration of an ultrasonic probe according to the first embodiment of the present invention. FIG. 2 is a view illustrating an internal configuration of the tip section of an ultrasonic probe according to the first embodiment of the present invention. FIGS. 3A through 3E are views for explanatorily illustrating the fixing of a wire to a swing pulley in an ultrasonic probe relating to the first embodiment of the present invention. FIGS. 4A and 4B are views for explanatorily illustrating the fixing of a wire to a drive pulley in an ultrasonic probe relating to the first embodiment of the present invention.

At first, an ultrasonic probe relating to the first embodiment of the present invention is described referring to FIG. 1. As shown in FIG. 1, the ultrasonic probe is comprised of a grip section 1 and an insert section 2 that includes a tip section 3. A motor 5 generating power for swinging an ultrasonic transducer unit 4 and an encoder 5a used for detecting the position angle of the ultrasonic transducer unit 4 are provided in the grip section 1. In the insert section 2 except for the tip section 3, a shaft 10 for transmitting the power of the motor 5 is provided. A drive pulley 6 connected to the shaft 10, a swing pulley 7 provided at the rotation shaft 9 of the ultrasonic transducer unit 4, a connecting section 11 connecting a wire 8 to the swing pulley 7, a position angle adjustment section 12 where the opposite end of the ring-shaped wire 8 opposed to the fixed end connected to the swing pulley 7 is connected to the drive pulley 6, intermediate pulleys 13 and 14 transmitting the rotating operation (hereinafter, called rotation) of the drive pulley 6 to the swing pulley 7, and a tension mechanism 15 for taking the slack away from the wire 8 are provided in the base section 3a of the tip section 3. In this example, although the wire 8 is used as a means for transmitting the power of the drive pulley 6 to the swing pulley 7, it is not intended to be limited to this example. And a structure, which has a cable shape, and similar function to the wire 8 may also be practically used.

Next, the operation of each of the components constituting the ultrasonic probe according to the first embodiment of the present invention described in FIG. 1 will be explained using FIGS. 1 and 2. An operator grasps the grip section 1 and inserts the insert section 2 into a living body cavity. The drive pulley 6 connected to the shaft 10 is driven to rotate by using the motor 5 to which power is supplied, the rotating operation of the drive pulley 6 being transmitted to the swing pulley 7 by the wire 8 through the intermediate pulleys 13 and 14, and the swinging operation of the ultrasonic transducer unit 4 is performed around the rotation shaft 9. Only one each of the intermediate pulleys 13 and 14 can be seen, respectively, in FIG. 2 but the respective ones consist of pairs, respectively. The wire 8 is engageably attached to each of the intermediate pulleys 13 and 14. The intermediate pulleys 13 and 14 are not intended to be limited to two and it may be possible a case where only one or more than three intermediate pulleys are arranged. The tension mechanism 15 in which the intermediate pulley 14 is mounted enables the removal of any slack from the wire 8 and the application of tension at the same time by pulling the intermediate pulley 14 in the direction of the arrow 16, for instance, by tightening a screw. The tension mechanism 15 may have a spring.

When a stepping motor is used for constituting the motor 5, the position angle of the ultrasonic transducer unit 4 can be detected by using the number of pulse inputs to the stepping motor and the ratio of diameters of the drive pulley 6 and the swing pulley 7. Additionally, in the case where the encoder 5a is provided, it can be detected by using the detected angle of the encoder 5a and the ratio of diameters of the drive pulley 6 and the swing pulley 7. The ultrasonic transducer unit relating to the first embodiment of the present invention is for the case when the axis direction of the drive pulley 6 and the axis direction of the rotation shaft 9 are intersecting.

Next, the attaching of the wire 8 and the adjustment of the origin position angle of the ultrasonic transducer unit 4 and the motor 5 will be described. First of all, the origin position angle of the swing pulley 7 on which the ultrasonic transducer unit 4 is mounted is determined as well as the origin position angle of the drive pulley 6 to which the shaft 10 connected to the motor 5 is attached. Then, the wire 8 is attached to the swing pulley 7 by the connecting section 11 and the wire 8 is stretched over the intermediate pulleys 13 and 14 and is wound around the drive pulley 6. Next, the wire 8 is fixed to the drive pulley 6 by the position angle adjustment section 12. In this manner, the respective origin position angles of the swing pulley 7 and the drive pulley 6 can be adjustably brought into coincidence with one another. Accordingly, the origin position angle of the ultrasonic transducer unit 4 and the origin position angle of the motor 5 can be adjusted to be brought into registration.

Therefore, since the wire 8 is fixed to the drive pulley 6 and the swing pulley 7, the wire 8 does not slip on each pulley and displacement can be reduced. Moreover, since the wire 8 is made in a ring-shape, the wire 8 can be attached only by hanging on each pulley, so that it can be easily laid down between the pulleys. Furthermore, the adjustment of the origin position angle of the ultrasonic transducer unit 4 becomes possible even after mounting of the ultrasonic transducer unit 4 onto the rotation shaft 9 due to the position angle adjustment section 12 provided in the drive pulley 6. Herein, the aforementioned ring-shape of the wire 8 is not only a ring-shape in the case when both ends of the continuous unbroken wire 8 are attached to the connecting section 11 but also one which includes the case where it is essentially ring-shaped. That is, it includes a ring-shape made by separating one continuous unbroken wire 8 into two individual pieces and fixing each of both ends of the two individual pieces of wire 8 to the drive pulley 6 and the swing pulley 7, respectively.

Herein, the fixing of the wire to the swing pulley 7 and the drive pulley 6 will be described with reference to FIGS. 3A through 4B. First of all, the fixing of the wire 8 to the swing pulley 7 is explained. As shown in FIG. 3A, the fixed side wall 11a of the connecting section 11 on which both ends of the wire 8 are fixed is mated with the cut section 18 of the swing pulley 7 shown in FIG. 3B and fixedly secured by using a screw 17 and so on, as shown in FIG. 3C. Moreover, for instance, an adhesive, solder, and the like are used as a means for fixing both ends of the wire 8 to the connecting section 11. Furthermore, the number of screws 17 is not intended to be limited to two and it may be possible to have one or three or more. Therefore, since the wire 8 can be tightly fixed to the swing pulley 7 by securing the fixed side wall 11a together with the cut section 18, it is possible to reduce the lift and the slippage of wire 8 on the swing pulley 7.

Figure 3D:
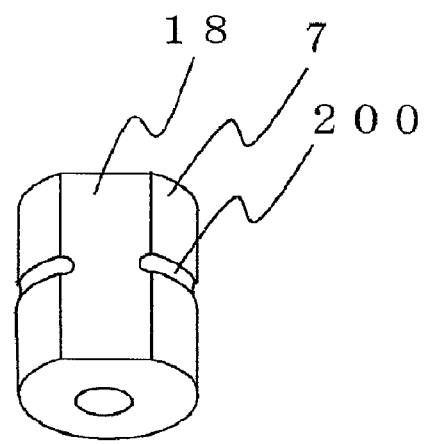
FIG. 3D A schematic perspective view illustrating a groove provided on the circumference of a swing pulley for permitting the wire of the ultrasonic probe according to the first embodiment of the present invention to be placed.
Figure 3E:
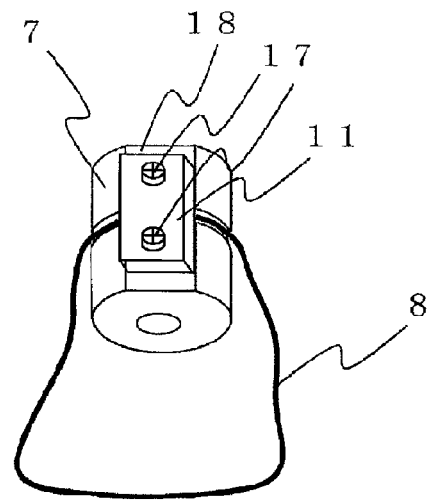
FIG. 3E A schematic perspective view illustrating a connecting section where the wire is fixed to the fixed side wall being attached to the cut section of the swing pulley having the groove where the wire is placed in an ultrasonic probe according to the first embodiment of the present invention.
Figure 4A:
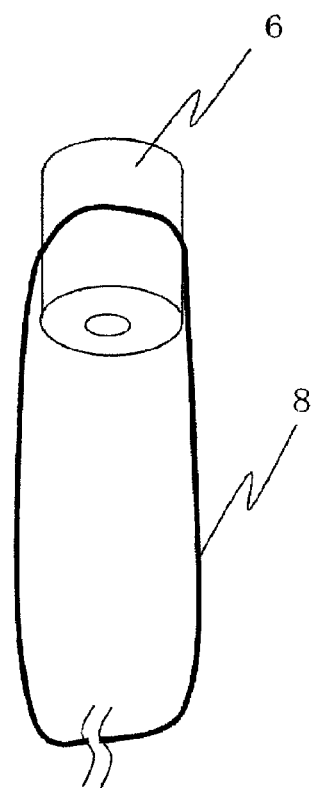
FIG. 4A A schematic view illustrating a drive pulley on which the wire is placed in an ultrasonic probe according to the first embodiment of the present invention.
Figure 4B:
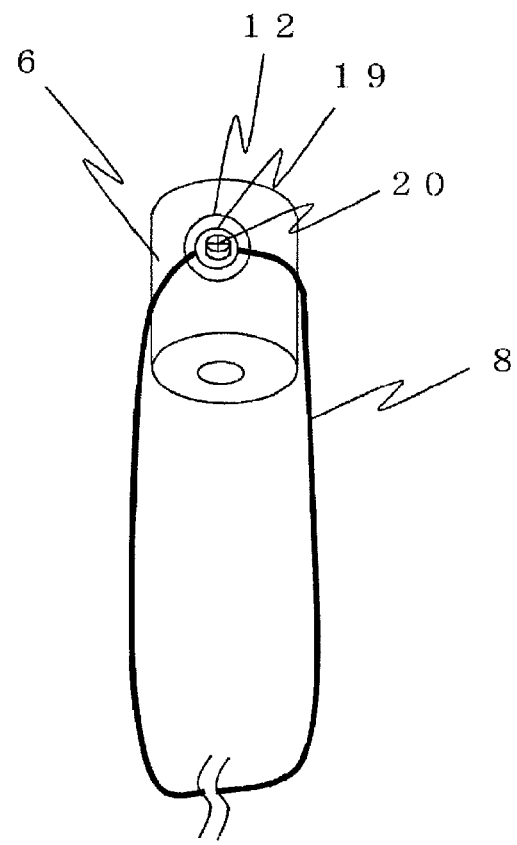
FIG. 4B A schematic view illustrating a drive pulley where a wire is fixed by clamping a screw through a plate-like portion in an ultrasonic probe according to the first embodiment of the present invention.

As shown in FIG. 3D, a groove 200 may be provided to extend along the circumference of the swing pulley 7 for placing the wire 8 therein, and the wire 8 can be securely fit in the groove 200 as shown in FIG. 3E, so that it is possible to reduce further the lift and the slippage of wire 8 on the swing pulley 7. Additionally, although the fixing of the wire 8 to the connecting section 11 has been explained herein, the fixing of the wire 8 may be accomplished in the same manner to the position angle adjustment section 12 instead of the connecting section 11.

On the other hand, the fixing of the wire 8 to the drive pulley 6 will be described with reference to FIGS. 4A and 4B. As shown in FIG. 4A, the wire 8 is hung on the drive pulley 6, which has been brought into registration with the origin position angle of the motor 5, and as shown in FIG. 4B, the wire 8 is fixed to the drive pulley 6 by clamping the wire 8 via the plate-like portion 19 by tightening the screw 20. Although the position angle adjustment section 12 is a screw-type in this example, it is not intended to be limited in this manner. Moreover, although the plate-like portion 19 is in the shape of a circle, it is not intended to be limited in this manner and it is possible for it to have a different shape. Furthermore, the number of screws 20 is not intended to be limited to one and it may be possible to have two or more. According to such a configuration of tightening the screw 20, it is possible for the origin position angle of the ultrasonic transducer unit 4 to be adjustably brought into registration with the origin position angle of the motor 5, and thereafter they can be securely fixed together.

Therefore, according to the first embodiment of the present invention, displacement of the wire 8 due to slippage on the pulley can be reduced by fixing both ends of the wire 8 to the swing pulley 7 and fixing the opposite end of the ring-shaped wire 8 to the drive pulley 6 at the position angle adjustment section 12, and the wire 8 can be easily mounted between the pulleys while carrying out adjustment of the origin position angle of the ultrasonic transducer unit 4 at the position angle adjustment section 12, and also shortening of the length of the wire 8 can be achieved.

Second Embodiment

Figure 5A:
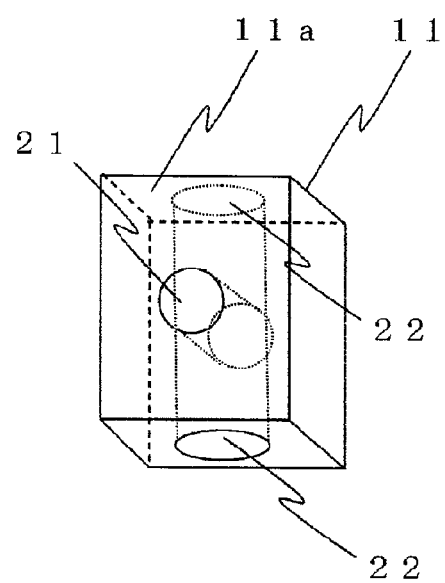
FIG. 5A A schematic view illustrating a connecting section having holes penetrating the center section and side wall section in an ultrasonic probe according to the second embodiment of the present invention.
Figure 5B:
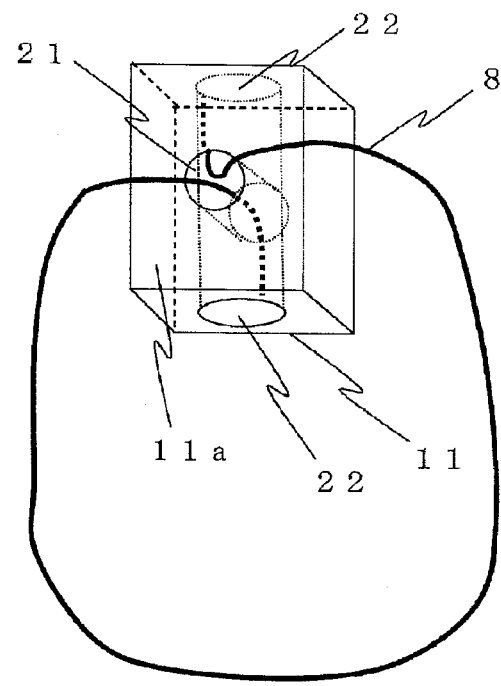
FIG. 5B A schematic view illustrating a connecting section where a wire is drawn from a hole of the center section and both ends of the wire are respectively drawn through the upper part and lower part of the hole in the ultrasonic probe according to the second embodiment of the present invention.
Figure 5C:
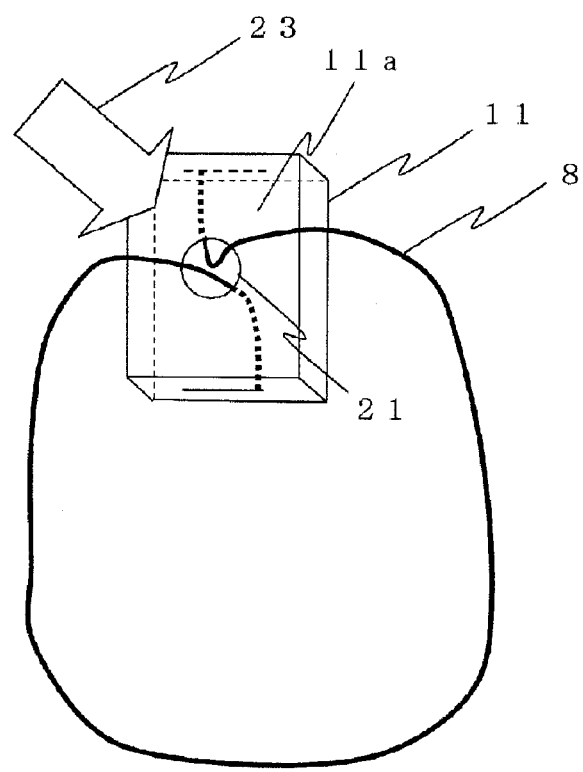
FIG. 5C A schematic view illustrating a connecting section where the hole is flattened by pressing to become one with the wire in the ultrasonic probe according to the second embodiment of the present invention.
Figure 6A:
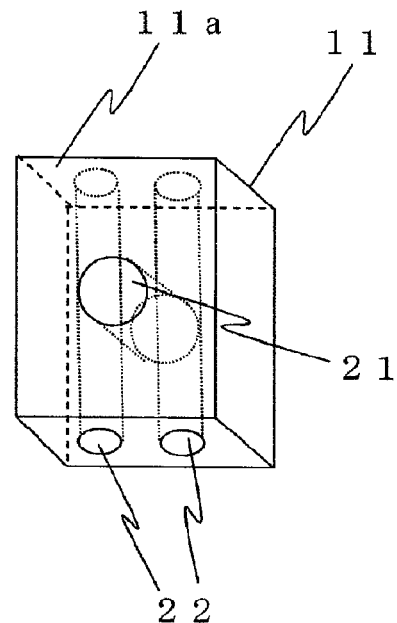
FIG. 6A A schematic view illustrating a connecting section where the number of holes becomes three in the ultrasonic probe according to the second embodiment of the present invention.
Figure 6B:
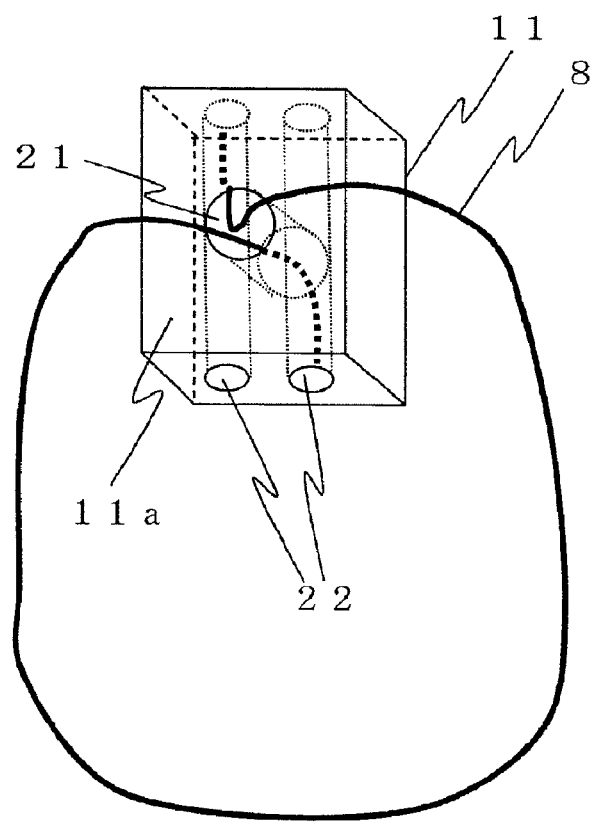
FIG. 6B A schematic view illustrating a connecting section where both ends of a wire drawn through the hole are inserted into the upper part and the lower part of the hole, respectively, in the ultrasonic probe according to the second embodiment of the present invention.
Figure 6C:
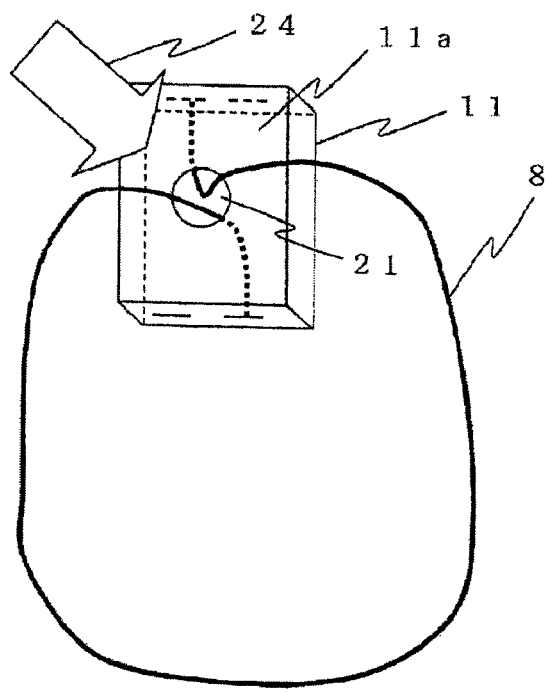
FIG. 6C A schematic view illustrating a connecting section where a hole is flattened by pressing to become one with a wire in the ultrasonic probe relating to the second embodiment of the present invention.
Figure 7:
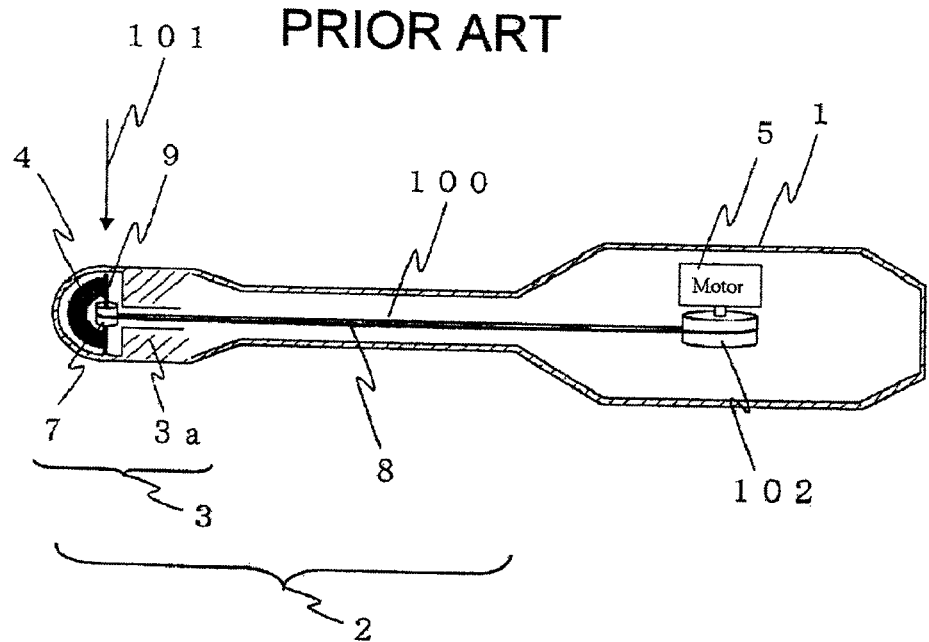
FIG. 7 A schematic view illustrating a configuration of an ultrasonic probe according to the prior art.
Figure 8:
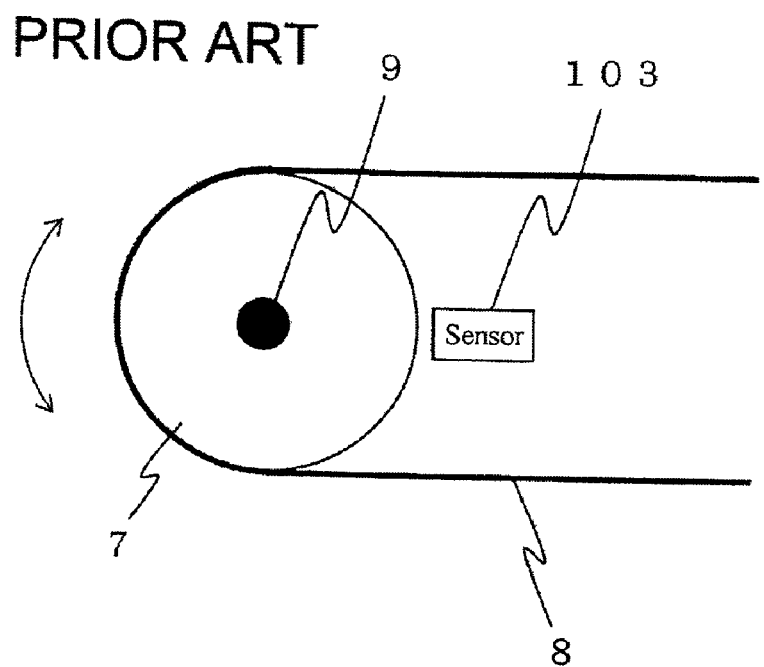
FIG. 8 A schematic view illustrating an internal configuration of the tip section of the ultrasonic probe according to the prior art.

Hereinafter, an ultrasonic probe according to the second embodiment of the present invention will be described with reference to FIGS. 5A through 6C. FIGS. 5A, 5B, and 5C are drawings to explain the fixing of the wire to the swing pulley in an ultrasonic probe of the second embodiment of the present invention. FIGS. 6A, 6B, and 6C are drawings to explain the fixing of the wire to the swing pulley in an ultrasonic probe of the second embodiment of the present invention, similar to FIGS. 5A, 5B, and 5C. As shown in FIG. 5A, the connecting section 11 is comprised of a member being deformed by an external force and has holes 21 and 22 penetrating the center section and the side wall section. As shown in FIG. 5B, the wire 8 is permitted to pass into from the hole 21 of the center section and both ends of the wire 8 passed are respectively permitted to pass through the upper part and the lower part of the hole 22. As shown in FIG. 5C, the connecting section 11 into which the wire 8 passes is compressed in the direction of arrow 23, resulting in the hole 22 being squashed and flattened to become one with the wire 8. Accordingly, the wire 8 becomes ring-shaped.

As mentioned above, a portion of the wire 8 squashed and flattened within the connecting section 11 can be made longer by passing the wire 8 not only through the hole 21 at the center section but also through the hole 22 at the side wall section, so that it is possible to reduce possibility of slipping of the wire 8 and coming out of the connecting section 11. Moreover, the wire 8 can be fixed closely to the swing pulley 7 due to the construction of the wire 8 coming out of the hole 21, so that it is possible to reduce the lift and the slippage of the wire 8 on the swing pulley 7. Although the wire 8 is fixed at the connecting section 11 in this example, the fixing of the wire 8 may be achieved in the same manner at the position angle adjustment section 12 instead of at the connecting section 11.

FIGS. 6A, 6B, and 6C are considered to be the same as FIGS. 5A, 5B, and 5C. As shown in FIG. 6A, the point where FIGS. 6A, 6B, and 6C differ from FIGS. 5A, 5B, and 5C is that the number of holes 22 provided at the connecting section 11 becomes two. Moreover, as shown in FIG. 6B, another differing point is in that both ends of the wire 8 drawn through the hole 21 are inserted into the upper part and the lower part of the hole 22, respectively. However, as shown in FIG. 6C, the point where a compression force is applied to the connecting section 11 in the direction of arrow 24 is the same as in FIG. 5C and the effect is also the same. Thus, according to the second embodiment of the present invention, it is possible to reduce slipping of the wire 8 and it's pulling out of the connecting section 11.

INDUSTRIAL APPLICABILITY

An ultrasonic probe of the present invention can prevent the position thereof from being displaced due to the slippage of a wire on a drive pulley and a swing pulley while swinging, it enables the easy attaching of the wire thereto while adjusting the origin position angle of an ultrasonic transducer unit in swing operation without using a position angle sensor, and it enables the length of the wire to be shortened, so that it is useful for an ultrasonic probe for emitting ultrasonic waves in a living organism and receiving echo signals while inserting an ultrasonic transducer unit into a living body cavity.

The invention claimed is:

1. An ultrasonic probe comprising;
   an ultrasonic transducer unit emitting ultrasonic waves while swinging,
   a motor, the motor adapted to generate power for swinging said ultrasonic transducer unit,
   a first power transmission device, the first power transmission device connected to a rotating shaft of said motor and transmitting said power,
   a drive device connected to said first power transmission device, the drive device rotated by said transmitted power,
   a cable-like second power transmission device, the cable-like second power transmission device adapted to transmit said power by the rotation of said drive device, wherein the second power transmission device includes a fixed end and an opposite end,
   a swing device, on which said ultrasonic transducer unit is mounted, swinging said ultrasonic transducer unit with said power due to the rotation of said drive device transmitted through said second power transmission device,
   a first fixing device to which the fixed end of the second power transmission device is fixed and which is removably, fixedly attached to said swing device together with said second power transmission device, and
   a second fixing device fixing, to said drive device, the opposite end of said second power transmission device, which is opposed to the fixed end that is fixed at the first fixing device, wherein an axis direction of the drive device and an axis direction of the rotation shaft of the ultrasonic transducer unit are configured to intersect.

2. The ultrasonic probe according to claim 1,
   wherein said first fixing device includes a material capable of being deformed by an external force and having a plurality of penetrating holes that are interconnected with one another inside thereof,
   wherein the first fixing device is applied thereto with a compressing force under a condition where ends of said second power transmission device are permitted to pass from one hole of said plurality of penetrating holes to another, to thereby be integrally fixed together with said second power transmission device, said first fixing device being fixed to said swing device together with said fixed second power transmission device.

3. The ultrasonic probe according to claim 1,
   wherein said second fixing device comprises a screw that tightens said second power transmission device to said drive device.

4. The ultrasonic probe according to claim 3,
   wherein said screw is provided with a plate-like portion, which is provided for preventing said second power transmission device from being damaged due to tightening of said screw.

5. The ultrasonic probe according to claim 1, including at least one intermediate pulley device adapted to remove slack from the second power transmission device by being movable in a direction towards and away from the drive device.

6. The ultrasonic probe according to claim 5,
   wherein the at least one intermediate pulley device is configured to move in a direction parallel to the swing device for removing any slack from the second power transmission device.

7. The ultrasonic probe according to claim 1, wherein the cable-like second power transmission device includes a wire.

8. The ultrasonic probe according to claim 1, further including at least one fastener configured to attach the first fixing device to the swing device.

9. The ultrasonic probe according to claim 8, wherein each of the at least one fastener comprises a screw.

10. The ultrasonic probe according to claim 1, wherein the second fixing device is configured to perform a simultaneous adjustment of origin position angle of the ultrasonic transducer unit and the motor.

11. An ultrasonic probe comprising:
    an ultrasonic transducer unit emitting ultrasonic waves while swinging;
    a motor;
    a shaft attached to the motor, the shaft adapted to be rotated by the motor;
    a drive pulley connected to the shaft, the drive pulley adapted to be rotated by the shaft;
    a swing pulley attached to a rotation shaft of the ultrasonic transducer unit; and
    at least one intermediate pulley positioned between the swing pulley and the drive pulley, the rotating operation of the drive pulley being transmitted to the swing pulley by a wire through the at least one slidable intermediate pulley, wherein the at least one slidable intermediate pulley is configured to slide in a direction towards and away from the drive pulley and in a direction parallel to the rotation shaft of the ultrasonic transducer unit;
    wherein the wire is fixed to the drive pulley and swing pulley.

12. The ultrasonic probe according to claim 11, wherein the wire is attached to the swing pulley by a connecting section.

13. The ultrasonic probe according to claim 12, wherein one or more screws attaches the connecting section to the swing pulley.

14. The ultrasonic probe according to claim 13, wherein the connecting section is configured to deform.

15. The ultrasonic probe according to claim 14, wherein the connecting section includes one or more holes penetrating therethrough, further wherein the wire passes through the one or more holes and the one or more holes are compressible.

16. The ultrasonic probe according to claim 11, wherein the at least one slidable intermediate pulley is configured to move in a direction parallel to the rotation shaft of the ultrasonic transducer unit and in a direction perpendicular to the shaft attached to the motor.

17. The ultrasonic probe according to claim 11, further including a fixing section fixing, to the drive pulley, one of the fixed end or the opposite end of a wire, which is configured to perform a simultaneous adjustment of origin position angle of the ultrasonic transducer unit and the motor.

18. An ultrasonic probe comprising;
   an ultrasonic transducer unit emitting ultrasonic waves while swinging,
   a motor, the motor adapted to generate power for swinging said ultrasonic transducer unit,
   a first power transmission device, the first power transmission device connected to a rotating shaft of said motor and transmitting said power,
   a drive device connected to said first power transmission device, the drive device rotated by said transmitted power,
   a cable-like second power transmission device, the cable-like second power transmission device adapted to transmit said power by the rotation of said drive device, wherein the second power transmission device includes a fixed end and an opposite end,
   a swing device, on which said ultrasonic transducer unit is mounted, swinging said ultrasonic transducer unit with said power due to the rotation of said drive device transmitted through said second power transmission device,
   a first fixing device to which the fixed end of the second power transmission device is fixed and which is fixedly attached to said swing device together with said second power transmission device, wherein said first fixing device includes a plurality of penetrating holes that are interconnected with one another inside thereof and the second power transmission device is configured to pass into at least one of the plurality of penetrating holes, and
   a second fixing device fixing, to said drive device, the opposite end of said second power transmission device, which is opposed to the fixed end that is fixed at the first fixing device.

* * * * *